United States Patent [19]
Uritsky et al.

[11] Patent Number: 5,870,187
[45] Date of Patent: Feb. 9, 1999

[54] METHOD FOR ALIGNING SEMICONDUCTOR WAFER SURFACE SCANS AND IDENTIFYING ADDED AND REMOVED PARTICLES RESULTING FROM WAFER HANDLING OR PROCESSING

[75] Inventors: Yuri Uritsky, Newark, Calif.; Patrick D. Kinney, Coon Rapids, Minn.; Man-Ping Cai, Campbell, Calif.

[73] Assignee: Applied Materials, Inc., Santa Clara, Calif.

[21] Appl. No.: 907,589

[22] Filed: Aug. 8, 1997

[51] Int. Cl.[6] .................................................. G01N 21/00
[52] U.S. Cl. ............................................ 356/237; 356/398
[58] Field of Search .................................... 356/372, 375, 356/394, 237, 239, 398, 431, 399, 400; 250/559.42, 559.48

[56] References Cited

U.S. PATENT DOCUMENTS

| | | | |
|---|---|---|---|
| 5,422,724 | 6/1995 | Kinney et al. | 356/375 |
| 5,479,252 | 12/1995 | Worster et al. | 356/237 |
| 5,497,007 | 3/1996 | Uritsky et al. | 250/491.1 |
| 5,565,979 | 10/1996 | Gross | 356/237 |
| 5,640,238 | 6/1997 | Nakano et al. | 356/237 |

*Primary Examiner*—Hoa Q. Pham
*Attorney, Agent, or Firm*—Thomason & Moser

[57] ABSTRACT

An automated method for aligning wafer surface scan maps and locating defects such as particle contaminant distributions on a wafer surface. More specifically, the invention is an automated method for locating added and removed contaminants and other defects on a semiconductor wafer surface after the wafer has undergone wafer-handling and/or processing. A second data set of a second scan of a wafer surface is misalignment-corrected to a first coordinate system of a first scan of the wafer surface. Thereafter, a final match is made between a first data set of the first scan and the misalignment-corrected data of the second scan. Non-matching locations in the misalignment-corrected data of the second scan represent added defects on the surface of the wafer. Non-matching locations in the base data of the first scan represent removed defects from the surface of the wafer.

8 Claims, 4 Drawing Sheets

METHOD FOR ALIGNING SEMICONDUCTOR WAFER SURFACE SCANS AND IDENTIFYING ADDED AND REMOVED PARTICLES RESULTING FROM WAFER HANDLING OR PROCESSING

BACKGROUND OF THE DISCLOSURE

1. Field of the Invention

The invention relates to semiconductor wafer characterization equipment and, more particularly, to techniques for determining the number and location of defects such as contaminant particles that have been added or removed on a semiconductor wafer after semiconductor wafer handling or processing.

2. Description of the Background Art

Semiconductor wafer characterization typically involves a scanning process for locating defects on the surface of a semiconductor wafer. A scanning device, e.g., a laser scanner, scans the entire wafer surface to provide a general overview of the semiconductor surface and locates defects such as contaminant particles on the wafer surface. One such laser scanner device is the Tencor SurfScan 6200, manufactured by Tencor Instruments.

Specifically, the laser scanner device raster scans the wafer surface with a laser beam to locate defects on the wafer surface by analyzing laser backscatter from defects on the surface. The laser scanner device creates a laser scan map of the coordinates of the wafer features and contaminant particles. This laser scan map uses the coordinate system of the laser scanner device to identify the location of surface features and particles. The manner in which the laser beam is scattered from the wafer surface features and particles yields signals from which estimated defect locations in terms of x and y coordinates can be determined.

To characterize a wafer process, successive scans of the same wafer are typically taken during semiconductor wafer processing. For example, prior to processing, the scanning system, under computer control, scans and creates a first scan map of the entire surface of the semiconductor wafer. The initial scan generates a first data set of surface data of contaminant locations on the wafer surface at the time of the initial scan. Thereafter, the wafer undergoes a second scan after processing and/or wafer handling. A second scan map is created from the post-process scan. The second scan generates a second data set of surface data of contaminant locations on the wafer surface at the time of the second scan. Comparing the scans should identify pre-process particles from process-related particles; however, since the position of the wafer on the scanner platen during the second scan is invariably different from the wafer position used during the first scan, successive scans of the same wafer have different misaligned sets of data. Simply subtracting the second scan from the first scan results in particles from the first scan identified as process-related particles. Consequently, the scanner erroneously indicates process-related particles that are not process-related.

Therefore, a need exists in the art for an automated method for aligning wafer surface scans to facilitate identification of additional particle contaminant locations on a wafer surface after wafer handling or process operations.

SUMMARY OF THE INVENTION

The disadvantages of the prior art are overcome by the present inventive method for aligning scan maps of particle distributions on a wafer surface. More specifically, the invention is an automated method for locating additional particle contaminants and other defects on a semiconductor wafer surface after the wafer has undergone wafer handling or processing.

The invention has as an input two scan maps. The first scan map having a data set x,y and a second scan map having data set x', y', where the second scan map is produced after a wafer handling and/or wafer processing step. The invention transforms the second data set x', y' of a second scan of the wafer surface to a coordinate system of the first scan of the wafer surface. The misalignment-corrected data set is hereinafter referred to as data set x", y". Thereafter, a final match is made between first data set x,y of the first scan and misalignment-corrected data set x", y". Non-matching locations in data set x", y" of the second scan represent added contaminant particles on the surface of the wafer. Non-matching locations in the base data x,y of the first scan represent removed contaminant particles that were removed from the surface of the wafer by the wafer handling or processing.

Utilization of this automated method locates added and removed defects such as process related contaminant particles on the surface of the wafer. As a result of using the invention after wafer processing or handling, process particles and defects arising during processing can be quickly and accurately located. Consequently, the sources of these defects can be readily identified. Also, since a scan is performed prior to processing and another scan is performed after processing, there is no need to use "clean" wafers to perform defect location. As such, previously contaminated wafers that would otherwise be discarded can be reused in the defect location process, thus decreasing the overall cost of system testing.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
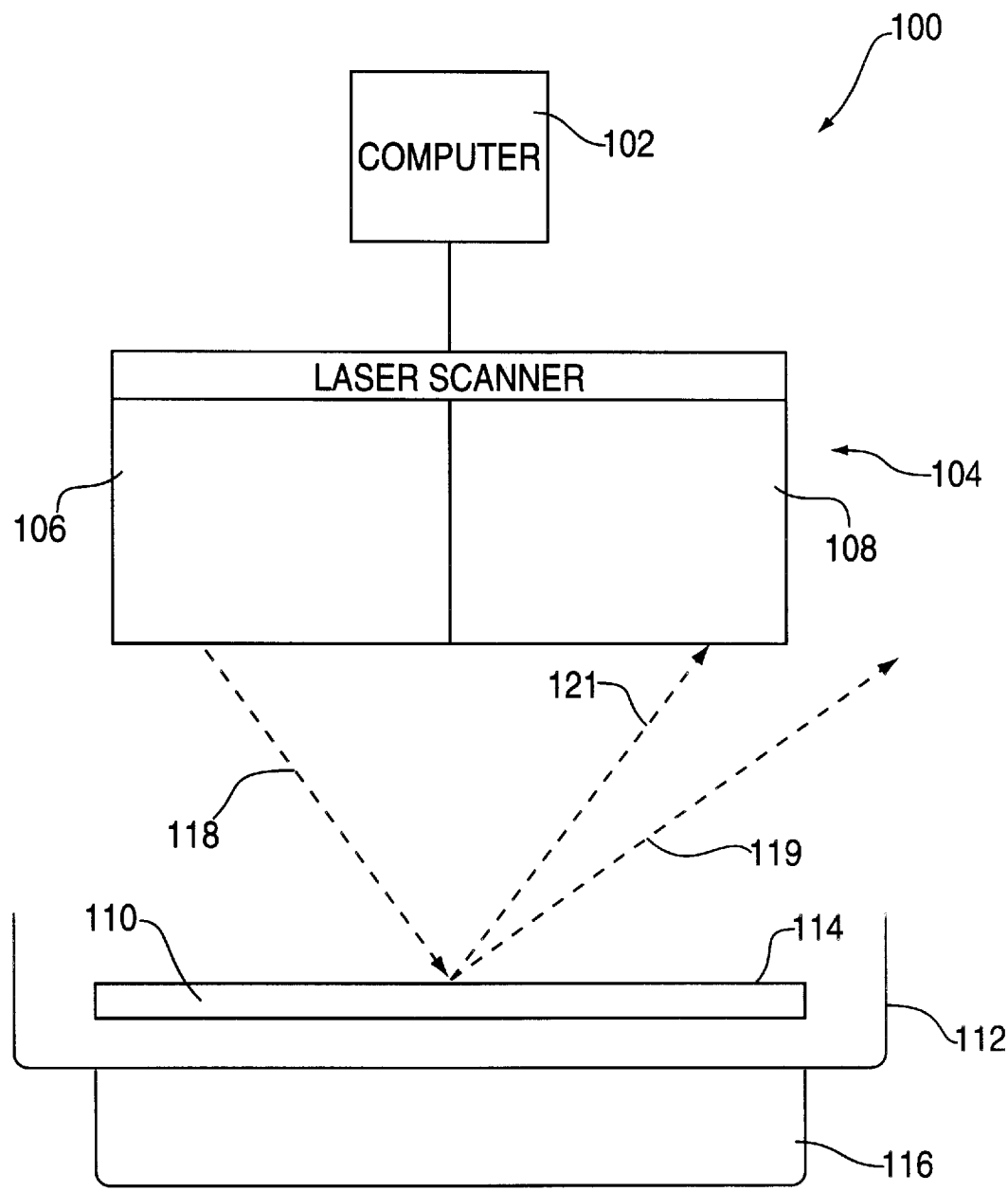
FIG. 1 depicts a block diagram of a laser scanner device that utilizes the invention.

FIG. 1 depicts a block diagram of an illustrative computer controlled laser scanner system 100 that utilizes the present invention. In accordance with a preferred embodiment of the invention, the system 100 utilizes an automated method for establishing the addition or removal of contaminant particles or other defects on a wafer 110 after wafer handling and/or wafer processing. A computer 102 generally controls operation of a laser scanner device 104. Specifically, the laser scanner device 104 contains a laser beam generator 106, a laser backscatter detector 108 and a stage 112 for supporting a semiconductor wafer 110. One example of such a laser scanner device is the Tencor SurfScan 6200, manufactured by Tencor Instruments. In operation, the computer 102 controls a laser beam 118 intensity, scan rate and position relative to a coordinate system of the stage. The coordinate system is a two-dimensional (x–y) coordinate system lying in the plane of the stage 112. The computer 102 also controls mechanical stage positioning equipment 116 that positions the stage beneath the scanning system to facilitate moving the wafer relative to the laser beam 118, i.e., scanning the wafer 114. Additionally, the computer 102 also collects and analyzes data from the detector 108.

In operation, the laser scanner device 104 linearly moves the stage 112 supporting the wafer 110 in a first direction and the laser is scanned using a moveable mirror to sweep the laser beam 118 across the surface 114 of the wafer in a second direction that is orthogonal to the first direction. As such, the laser scans the wafer in a raster scan pattern. The laser beam 118 generally reflects from the wafer along path 119 (i.e., along a path away from the detector 108) until the beam is incident upon a wafer defect that scatters the laser light (e.g., along path 121 into the detector 108). Scattered light signals from particles, features and other defects on the wafer surface are collected and used to deduce the coordinates of the defects. The computer 102 receives information regarding the detected scattered light from the detector 108 and automatically deduces the coordinate locations for these particles.

Figure 2:
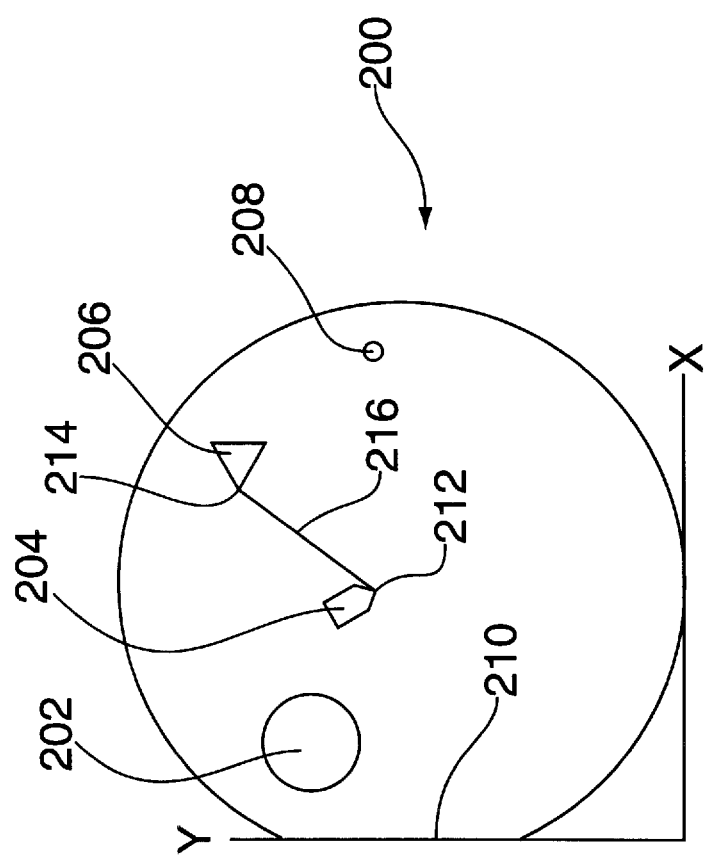
FIG. 2 depicts a top plan view of a wafer having contaminant particles on the surface of the wafer in a first coordinate system X, Y.
Figure 3:
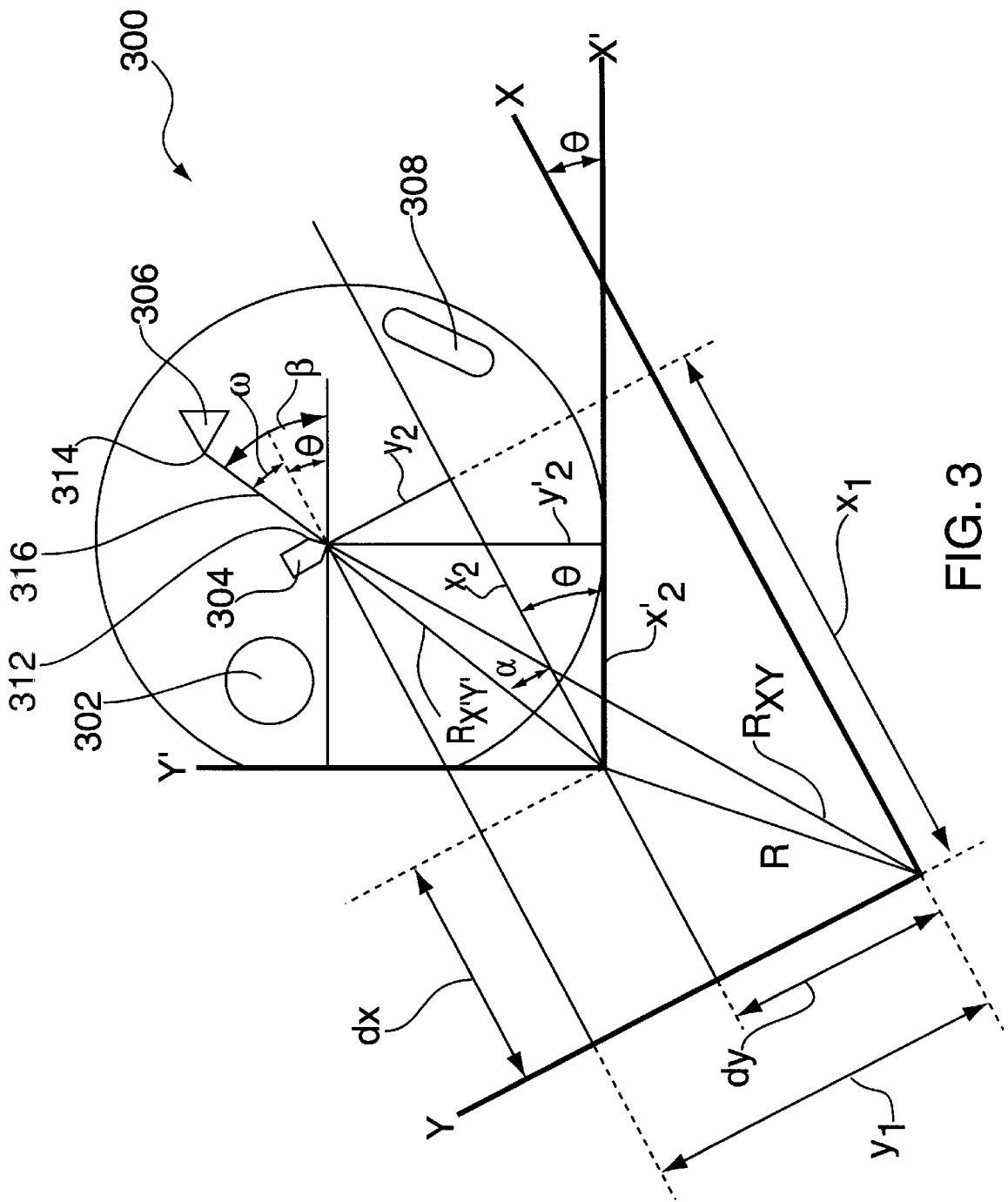
FIG. 3 depicts the wafer in FIG. 2 after wafer-handling having additional contamination in a second coordinate system X', Y' transformed to the first coordinate system X, Y.

Specifically, after scanning the wafer surface, a coordinate system is automatically established from the position of the edge of the wafer and a landmark on the wafer. For example, a landmark on six inch wafer typically is a flat segment 210 in the wafer's otherwise circular circumference, as shown in FIGS. 2 and 3. The laser scanner device 104 fixes the y axis coincident with the flat segment and the x axis tangent to the bottom of the wafer. Alternatively, for eight inch wafers a landmark is typically a notch in the wafer's otherwise circular circumference, the laser scanner device 104 fixes the coordinate system relative to the notch. The notch is fixed at the "12 o'clock" position and the X and Y axes are tangent to the wafer edge. Generally, the X-axis is parallel to a first line that extends through the notch and the center of the wafer, and the Y-axis is parallel to a second line extending from the wafer center, where the second line is orthoganal to the first line. Once the wafer coordinate system is established, all particles located by the laser scanner device 104 are referenced to the fixed coordinate system.

FIGS. 2 and 3 depict a wafer having two sets of data from two separate scans. Such sets of data of multiple scans of the same wafer are misaligned and differ due primarily to "discretization" errors, i.e., uncertainties arising from the discrete nature of the sampling process. The primary source of uncertainty arises from the discrete sampling grid approximation to particle locations. Since the size of the smallest sample cell is 28 $\mu$m×10 $\mu$m, the maximum error due solely from the discrete nature of the sampling process is 14 $\mu$m×16.5 $\mu$m. However, the laser scanner devices available in the art, although capable of sampling every 10 $\mu$m, only store data from every tenth sample, i.e., every 100 $\mu$m.

Another source of error is the construction of the coordinate system. Accordingly, determination of the landmark and wafer edge are subject to the same discretization errors. As discussed above, the coordinate system is established relative to a landmark and the edge on the wafer. The wafer is typically arbitrarily oriented in the laser scanning device, the x–y positions must be transformed to the established coordinate system. Thus, the location of the landmark must be precisely determined. For example, the notch in an eight inch wafer having a 200 mm diameter is only 1 mm×1 mm. If the angular position of the notch were located in error by 1°, the resulting error in particle positions would be 1,700 $\mu$m for particles near the wafer edge. Additionally, since the device records every tenth sample, only 5 to 10 samples are recorded in a 1 mm×1 mm notch. Such a small number of samples is not sufficient to repeatably determine the notch position and produce an accurate coordinate system using the notch as a landmark.

Errors in locating the landmark and the wafer edge may propagate to much larger errors after the particle coordinates are transformed to the established coordinate system using inaccurate edge and landmark data. Other coordinate uncertainties also exist and, in total, the uncertainties can produce an error area of as much as 100 $\mu$m by 100 $\mu$m.

A method in the art that is available to reduce such uncertainties resulting from discretization errors is a multiple-scan method for wafer particle analysis disclosed in commonly assigned U.S. Pat. No. 5,422,724 issued Jun. 6, 1996 and is herein incorporated by reference.

Figure 4:
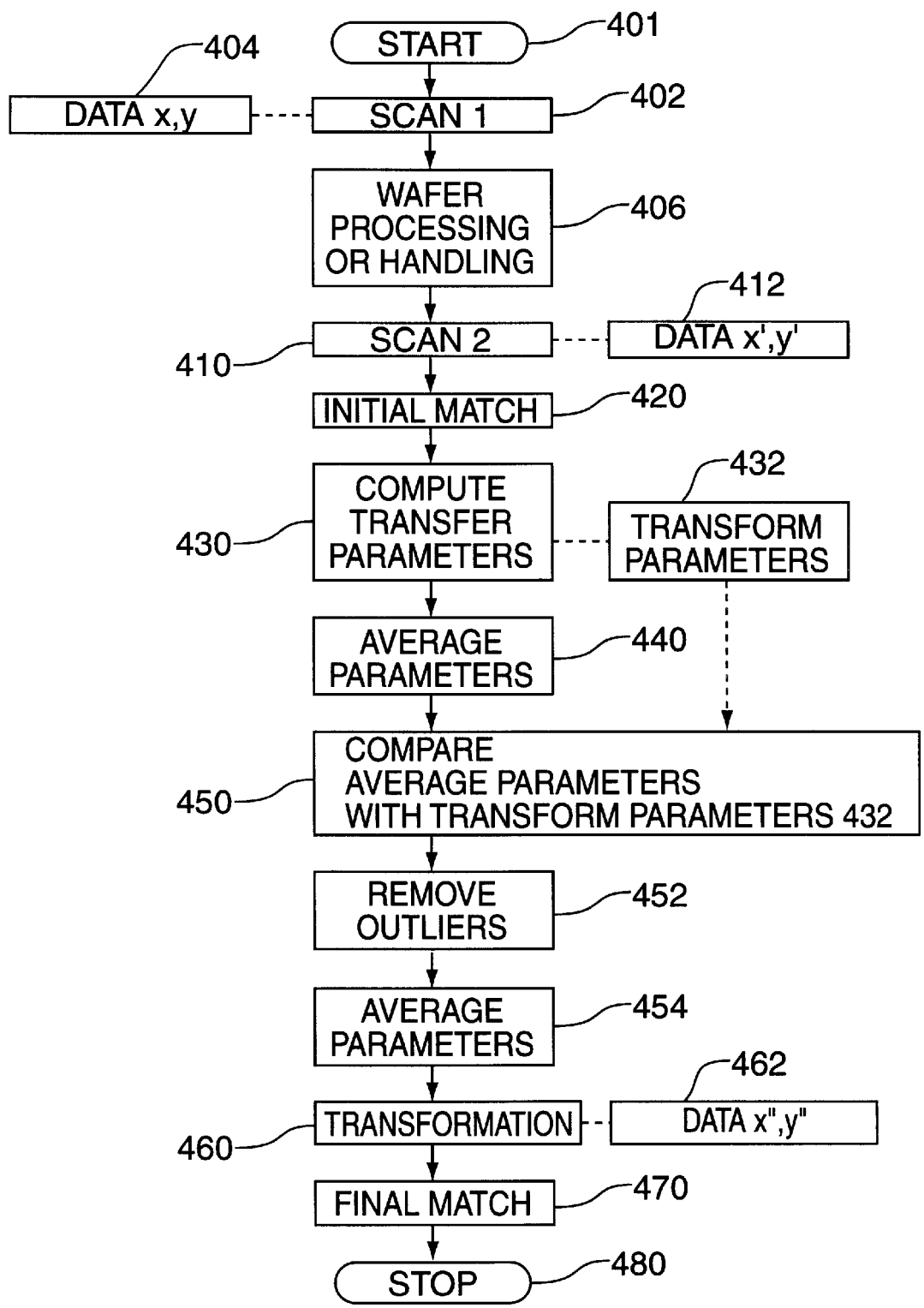
FIG. 4 depicts a flow chart of a method for aligning scan maps of particle distributions on a wafer surface in accordance with the present invention.

FIG. 4 depicts a flow chart of the inventive routine 400 of the present invention for aligning scan maps of particle distributions on a wafer surface. This routine is implemented as a software routine that is executed upon a general-purpose computer (e.g., computer 102 of FIG. 1). Although the routine is described below in the context of a software embodiment, any number of steps in the routine may be performed within a hardware device. In fact, the entire routine could be embodied within an application specific integrated circuit (ASIC). As such, the inventive routine should be broadly interpreted as being embodied in hardware, software or any combination of hardware and software that fulfills the general process steps discussed below.

The routine begins at step 401 and proceeds to step 402, where, prior to processing, a scanning system (e.g., system 102 in FIG. 1) scans the wafer surface and creates a first scan map of the surface of the semiconductor wafer. The initial scan generates and stores a first data set x,y 404 containing locations of contaminants (defects) on the wafer surface at the time of the initial scan. Thereafter, at step 410, the wafer undergoes a second scan, usually after processing or wafer handling step 406. A second scan map is created from the post-process scan and stored in memory. The second scan generates a second data set x', y' 412 containing locations of contaminants on the wafer surface at the time of the second scan. The data from both scans is temporarily stored in memory within the computer.

Although the x–y coordinate data for each of the two scans are transformed to a common coordinate system by using the landmark and the wafer edge to establish the x and y axes, the two sets cannot be precisely aligned because they were derived from scans made for different wafer orientations. However, the scans are first compared and transformation parameters are computed to transform the scans to a common coordinate system. This is generally accomplished by transforming the second scan, having coordinate system X', Y', to the first scan, having coordinate system X, Y.

Specifically, the method, at step 420, aligns the two scan maps, i.e., 200 and 300 of FIGS. 2 and 3, by first matching the locations of defects that appear in both scans. The defects located in both scans that match are identified by comparing x and y positions for a particular defect in one scan to within a selected distance (e.g., ±100 μm) of the position measured in the second scan, and the scattering areas of the detected defect (i.e., defect size) must be approximately the same, to within a selected difference area (e.g., within ±50 percent).

As discussed above, different scanning maps of the same wafer have different sets of data, i.e., each scan is unique such that each scan produces different x–y coordinates for the same defects. For example, an initial pre-process scan 200, as depicted in FIG. 2, generates a first data set x,y. The initial scan has contaminant particle areas 202, 204, 206, and 208 on the surface of the wafer. A second scan 300 of FIG. 3, usually a post-process scan, has a second data set x', y' with contaminant particle areas 302, 304, 306, and 308 on the surface of the wafer. Areas 208 and 308, respectively, represent removed and added contaminant particle areas.

Although the contaminant particle areas 202, 204, and 206 match 302, 304, and 306, respectively, the two sets of coordinates cannot be immediately compared because they were derived from separate orientations of the same wafer. Illustratively, the defect coordinates for map 200 are identified in coordinate system x,y and the defect coordinates in map 300 are identified in coordinate system x', y'. Therefore, the two scans must be first be aligned. Specifically, the data from one of the scans must be corrected to correct the difference between the coordinate systems of the two scans. The correction between the scans is accomplished by a coordinate transformation, to transform the data to the coordinate system of the other scan.

Aligning the two sets of x–y data first requires eliminating any differences between the coordinate systems associated with the two wafer scans. Any data relating to extraneous particles which either cannot be matched between the two scans, or which do not contribute to the transformation parameters is ignored. Thus, areas 208 and 308 which represent removed and added, respectively, contaminant particle areas are therefore ignored.

Transformation parameters are computed at step 430 for each pair of matching particles, i.e., two particles from one scan and two matching particles from the other scan, to compute coordinate transformation data. Since a first scan is unique and has a coordinate system independent of a second scan, coordinate transformations are performed during utilization of the inventive method. Transforming from one coordinate system to another can be considered to include a linear movement of the X and Y axes (along vector R in FIG. 3) that the new origin assumes a position displaced from the old origin, together with a rotation of the axis about the origin (along angle Θ in FIG. 3) to a new angular orientation. Such coordinate transformations are well known, and the equations for performing them may be found in almost any basic text on linear algebra, coordinate geometry, or related subject matter. For example, equations involved in performing such coordinate transformations can be found in a text by John J. Craig entitled "Introduction to Robotics: Mechanics and Control," 2nd edition, published by Addison-Wesley Publishing Company, Inc. (1989), and specifically on pages 25–30. Another text by Howard Anton entitled "Elementary Linear Algebra" published by Anton Textbooks, Inc. (1987), completely defines transformation equations on pages 229–230.

As shown in FIG. 3, the transformation is expressed as $(dx_i, dy_i, \Theta_i)$, where i is the selected number of areas having identifiable counterparts in the other scan map. As discussed above, there are a number of specific well-known methods that could be used to compute the particle pair transformation parameters $(dx_i, dy_i, \Theta_i)$ 432. For example, and for this discussion, the transformation can be expressed as a linear displacement of the X and Y axes and the angular rotation of the axes. In general, the transformation $(dx_i, dy_i, \Theta_i)$ is computed for every possible pair of matching particles, except that no transformation is computed unless the particles in a pair are more than a selected distance apart (e.g., 30 mm). From all the computed transformations, an average transformation is computed, by averaging the dx, dy and Θ values, and is designated $(dx_{avg}, dy_{avg}, \Theta_{avg})$, where $dx_{avg} = \Sigma dx_i/n$, $dy_{avg} = \Sigma dy_i/n$, and $\Theta_{avg} = \Sigma \Theta_i/n$, where n is the number of particle pairs analyzed.

Thus, at step 430, after identifiable counterparts, e.g., 202 and 302, 204 and 304, and 206 and 306, are selected, angle Θ is determined. Angle Θ is determined by the angle between the X, Y coordinate axes and the X', Y' coordinate axes, shown in FIG. 3. The relation between axes X, Y and X', y' is determined from points 212 and 214 located in selected areas 204 and 206 from the x, y data, shown in FIG. 2, and their identifiable counterparts 312 and 314 from the x', y' data in selected areas 304 and 306, shown in FIG. 3. The line 316 between 312 and 314 relates to the line 216 between 212 and 214 and angles β and ω, as shown in FIG. 3, are determined. Angles are computed using the equation defining an inverse tangent function of the general form:

$$\tan^{-1}[(y_{312}-y_{314})/(x_{312}-x_{314})]$$

The difference between angles β and ω, i.e., (β−ω), equates to the value of angle Θ.

The values for $dx_i$ and $dy_i$ are determined by displacement vector R, the value of angle Θ and Vectors $R_{XY}$ and $R_{X'Y'}$. Vectors $R_{X'Y'}$ and $R_{X,Y}$ define the position of each particle in the X, Y and X', Y' coordinate systems. R is determined by performing vector subtraction of $R_{X'Y'}$ and $R_{X,Y}$ $(R_{X'Y'}-R_{X'Y'})$. $R_{X,Y}$ is defined as $x_2'$ and $y_2'$, where these coordinates are measured horizontally and vertically from the particle 312. These coordinates are first expressed as corresponding values $x_2$ and $y_2$, which are parallel with the X, Y coordinate system, i.e., $x_1$ and $y_1$, before $x_2'$ and $Y_2'$ can be converted to the X, Y coordinate system. $R_{X'Y'}$ is determined by first determining the angle (Θ+α) between $R_{X'Y'}$ and the X' axis for the X, Y coordinate system which is equated by:

$$(\Theta+\alpha)=\tan^{-1}(y_2'/x_2'),$$

where $x_2'$ and $y_2'$ are the coordinates of $R_{X'Y'}$ in the X', Y' coordinate system and α=(Θ+α)−Θ. Then $x_2$ and $y_2$ are determined by:

$$X_2=|R_{X'Y'}|\cos\alpha-, Y_2=|R_{X'Y'}|\sin\alpha$$

where $|R_{X'Y'}|^2=(x_2')^2+(y_2')^2$.

Finally, dx and dy are computed as:

$$dx=x_1-x_2, dy=y_1-y_2.$$

Thereafter, at step 440, an average transformation parameter computation is performed using all the computed transformations. Specifically, the average is computed by averaging the dx, dy and Θ values, designated as $(dx_{avg}, dy_{avg}, \Theta_{avg})$. At step 450, the averaged transform parameters $(dx_{avg}, dy_{avg}, \Theta_{avg})$ are compared to each particle pair $(dx_i, dy_i, \Theta_i)$. If any of the particle pairs $(dx_i, dy_i, \Theta_i)$ differ dramatically from the averaged transform parameters $(dx_{avg}, dy_{avg}, \Theta_{avg})$, i.e., $dx_i \gg dx_{avg}$, $dy_i \gg dy_{avg}$, $\Theta_i \gg \Theta_{avg}$, the particle pair $(dx_i, dy_i, \Theta_i)$ differing dramatically is considered an "outliner". At step 452, the method removes any outliners (if any) in the particle pairs from the respective data sets. The average transformation is computed again at step 454 without the identified outliner particle pairs; thus, the method computes revised averaged transform parameters ($dx_{avg}'$, $dy_{avg}'$, $\Theta_{avg}'$). If necessary, outliners found in the second averaging step (step 454) may also be removed and the average again computed.

At step 460, the method transforms the second data set x', y' 412 of the second scan to the X, Y coordinate system of the first scan using the averaged transform parameters ($dx_{avg}$, $dy_{avg}$, $\Theta_{avg}$) or, if outliers were found at step 450, using the revised averaged transform parameters ($dx_{avg}'$, $dy_{avg}'$, $\Theta_{avg}'$). As such, the data coordinates of second data set x',y' are transformed to form data x", y" 462.

The method 400 then, at step 470, compares the two scan maps for matching and non-matching defect locations. A final match is made between data x,y 404 of the first scan and the misalignment-corrected data x", y" 462 of the second scan. Non-matching locations in the misalignment-corrected data x", y" 462 of the second scan represent contaminant particles added to the surface of the wafer during handling or processing. Non-matching locations in the base data x,y 404 of the first scan represent contaminant particles that were removed from the surface of the wafer during handling or processing. Specifically, non-matching locations of the misalignment-corrected data x", y" 462 of the second scan are represented by contaminant particle area 308 in FIG. 3. Area 308 represents added contaminant particles on the surface of the wafer. Non-matching locations in the base data, i.e., the first data set x,y 404 of the first scan, is represented by contaminant particle area 208 in FIG. 2. Area 208 represents removed contaminant particles from the surface of the wafer.

Utilization of this automated method for aligning semiconductor wafer surface scans accurately locates contaminant particles and other defects added or removed from the surface of a wafer after each process step. As a result of using the invention during processing of semiconductor wafers, process-particles and defects arising during processing can be quickly located and suppressed and/or eliminated to significantly decrease the number of defective wafers. Also, since a scan is performed prior to processing and another scan is performed after processing, there is no need to use "clean" wafers to perform defect location. As such, previously contaminated wafers that would otherwise be discarded can be reused in the defect location process, thus decreasing the overall cost of system testing.

The foregoing description illustratively transformed the first scan data set x,y into the coordinate system of the second scan data set x', y'. Of course, the second scan data set x', y' could be transformed into the coordinate system of the first scan data set x,y using the same technique described above.

Although various embodiments which incorporate the teachings of the present invention have been shown and described in detail herein, those skilled in the art can readily devise many other varied embodiments that still incorporate these teachings.

What is claimed is:

1. A method for aligning a first scan of a semiconductor wafer surface and a second scan of the semiconductor wafer surface, where the first scan contains first data set with respect to a first coordinate system and the second scan contains a second data set with respect to a second coordinate system, comprising the steps of:

(a) selecting matching areas of said first data set and said second data set;

(b) determining transformation parameters for said matching areas;

(c) transforming each data of said second data set from said second coordinate system to said first coordinate system, using said determined transformation parameters; and (d) identifying added defects and removed defects on said wafer surface, wherein said added defects are non-matching locations of said transformed second data set with said first data set, and said removed defects are non-matching locations of said first data set with said transformed second data set.

2. The method of claim 1 wherein step (b) further comprises the steps of:

computing a transformation parameter for each selected matching area;

averaging the transformation parameters to form an averaged transformation parameter.

3. The method of claim 2 wherein step (b) further comprises the step of:

comparing each transformation parameter with said averaged transformation parameter to identify an outlier and repeating said averaging step without said outlier for a revised averaged transformation parameters.

4. A method for aligning a first scan of a semiconductor wafer surface and a second scan of the semiconductor wafer surface, where the first scan contains a first data set with respect to a first coordinate system and the second scan contains a second data set with respect to a second coordinate system, comprising the steps of:

(a) selecting matching areas of said first data set and said second data set;

(b) computing a transformation parameter for each selected matching area;

(c) averaging the transformation parameters to form an averaged transformation parameter;

(d) comparing each transformation parameter with said averaged transformation parameter to identify an outlier and repeating said averaging step without said outlier for a revised averaged transformation parameter;

(e) transforming each data of said second data set from said second coordinate system to said first coordinate system, using said determined transformation parameters; and (f) identifying added particles and removed defects of said wafer surface, wherein said added defects are non-matching locations of said transformed second data set with said first data set, and said removed defects are non-matching locations of said first data set with said transformed second data set.

5. A method for aligning a first scan of a semiconductor wafer surface and a second scan of the semiconductor wafer surface, where the first scan contains first data set with respect to a first coordinate system and the second scan contains a second data set with respect to a second coordinate system, comprising the steps of:

(a) selecting matching areas of said first data set and said second data set;

(b) determining transformation parameters for said matching areas;

(c) transforming each data of said first data set from said first coordinate system to said second coordinate system, using said determined transformation parameters; and (d) identifying added defects and removed defects on said wafer surface, wherein said removed defects are non-matching locations of said transformed first data set with said second data set, and said added defects are non-matching locations of said second data set with said transformed first data set.

6. The method of claim 5 wherein step (b) further comprises the steps of:

computing a transformation parameter for each selected matching area;

averaging the transformation parameters to form an averaged transformation parameter.

7. The method of claim 6 wherein step (b) further comprises the step of:

comparing each transformation parameter with said averaged transformation parameter to identify an outlier and repeating said averaging step without said outlier for a revised averaged transformation parameters.

8. A method for aligning a first scan of a semiconductor wafer surface and a second scan of the semiconductor wafer surface, where the first scan contains a first data set with respect to a first coordinate system and the second scan contains a second data set with respect to a second coordinate system, comprising the steps of:

(a) selecting matching areas of said first data set and said second data set;

(b) computing a transformation parameter for each selected matching area;

(c) averaging the transformation parameters to form an averaged transformation parameter;

(d) comparing each transformation parameter with said averaged transformation parameter to identify an outlier and repeating said averaging step without said outlier for a revised averaged transformation parameter;

(e) transforming each data of said first data set from said first coordinate system to said second coordinate system, using said determined transformation parameters; and (f) identifying added particles and removed defects of said wafer surface, wherein said removed defects are non-matching locations of said transformed first data set with said second data set, and said added defects are non-matching locations of said second data set with said transformed first data set.

* * * * *